United States Patent [19]

Corvi-Mora

[11] 4,123,530
[45] Oct. 31, 1978

[54] N-CYCLOHEXYL-PIPERAZINO ACETAMIDES AND PROPIONAMIDES

[75] Inventor: Camillo Corvi-Mora, Milan, Italy

[73] Assignee: Camillo Corvi S.p.A., Piacenza, Italy

[21] Appl. No.: 758,725

[22] Filed: Jan. 12, 1977

[30] Foreign Application Priority Data

Jan. 23, 1976 [IT] Italy ................................ 19517 A/76

[51] Int. Cl.$^2$ .................. H61K 31/495; C07D 295/14
[52] U.S. Cl. ...................................... 424/250; 544/400
[58] Field of Search ...................... 260/268 R; 424/250

[56] References Cited

U.S. PATENT DOCUMENTS 3,652,568  3/1972  Winter et al. ..................... 260/268 R
3,658,821  4/1972  Fauran et al. ..................... 260/268 C

OTHER PUBLICATIONS

Masao Murakami et al., Chemical Abstracts, vol. 74, 99513g (1971).

Primary Examiner—Jose Tovar
Attorney, Agent, or Firm—Ladas, Parry, Von Gehr, Goldsmith & Deschamps

[57] ABSTRACT

New piperazine derivatives and homologs thereof of formula

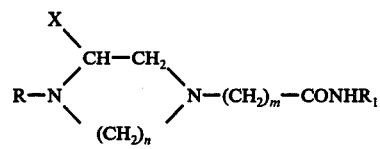

wherein $n$ is equal to 2 or 3 and $m$ to 1, 2 or 3;
x represents hydrogen or a methyl group
R represents hydrogen or a $C_1$ to $C_6$ lower alkyl group or a $C_1$ to $C_3$ hydroxyalkyl group; and
$R_1$ is one of the following groups:
a substituted cyclohexyl of formula

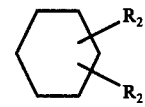

wherein $R_2$ is hydrogen or a $C_1$ to $C_6$ lower alkyl group,
a substituted phenyl of formula

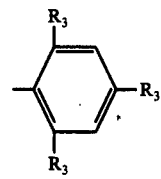

wheein $R_3$ is hydrogen, methyl or ethyl,
or wherein $R_1$ is norbornyl, bornyl or cinnamyl, are useful as antiulcerous compounds.

6 Claims, No Drawings

N-CYCLOHEXYL-PIPERAZINO ACETAMIDES AND PROPIONAMIDES

The present invention concerns new piperazine derivatives and homologs thereof of formula

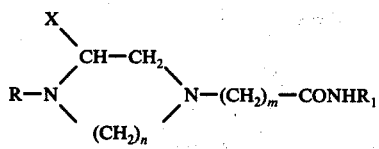

wherein $n$ is equal to 2 or 3 and $m$ to 1, 2 or 3;
X represents hydrogen or a methyl group;
R represents hydrogen or a $C_1$ to $C_6$ lower alkyl group or a $C_1$ to $C_3$ hydroxyalkyl group; and
$R_1$ is one of the following groups:
a substituted cyclohexyl of formula

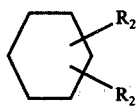

wherein $R_2$ is hydrogen or a $C_1$ to $C_6$ lower alkyl group,
a substituted phenyl of formula

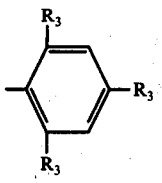

wherein $R_3$ is hydrogen, methyl or ethyl,
a norbornyl of formula

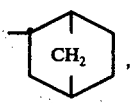

a bornyl of formula

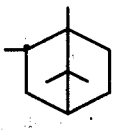

and
a cinnamyl of formula

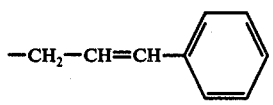

These compounds possess anti-ulcer and anti-secretion properties and are entirely free from anticholinergic activity.

These compounds can be prepared by first reacting an amine of formula $R_1$—$NH_2$ with an acyl chloride derivative (e.g. chloracetyl chloride, chloropropionyl chloride or chlorobutyryl chloride) and, thereafter, condensing the obtained product with piperazine or its derivatives. For instance, the following reaction can be performed:

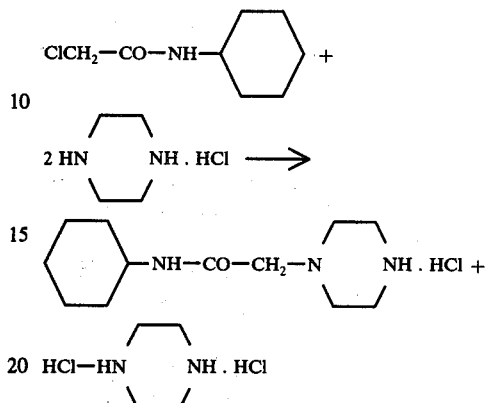

In such instance, one mole of N-(2-chloracetyl)-cyclohexylamine can be reacted with two moles of piperazine and two moles of HCl in water solution.

The reaction works also when 1 mole of piperazine dihydrochloride is used.

It is also possible to use an excess of piperazine in water in ratios of 1:3 to 1:4, however in such case the process is more expensive. On the other hand, the condensation can be carried out in organic solvents, e.g. chloroform or benzene.

The new compounds are also active in the form of their salts with organic or mineral acids, such as, for instance, hydrochlorides, sulfates, phosphates, maleates, succinates and tartrates.

The compounds of the present invention will be more fully described with reference to the following examples.

EXAMPLE 1

Anhydrous piperazine (178.28 g; 2 moles) was dissolved in 1000 ml distilled water. Then HCl 37% (166.6 ml) was added dropwise to provide 2 moles of piperazine mono-hydrochloride. Then N-(chloracetyl)-cyclohexylamine (175.66 g) was added to the above solution of the hydrochloride. The temperature rose to 100° C. and the reaction was completed by refluxing for two hours.

After cooling, the reaction mixture was made alkaline with a 35% NaOH solution and thereafter extracted with chloroform.

The chloroform extract was washed with water, dried with anhydrous $Na_2SO_4$, filtered and evaporated.

The residue was washed with petroleum ether, drained and dried.

The obtained 1-piperazinyl-4-methylene carbonylcyclohexylamine (or N-[1-piperazinylacetyl]-cyclohexylamine), code C/63, was distilled under reduced pressure (b.p. 190° C./0.5 mm); m.p. 111°–112°; yield 65% of theory.

Analysis: Calculated for $C_{12}H_{23}N_3O$: C 63.96; H 10.29; N 18.65; Found: C 63.93; H 10.18; N 18.67

IR Spectrum (1% in KBr), characteristic absorptions:
3320 $cm^{-1}$ (NH amido stretching); 3200 $cm^{-1}$ (NH imino stretching); 2930, 2850 $cm^{-1}$ (CH stretching);

1640, 1520 cm$^{-1}$ (CO stretching); 1450, 1330, 1260, 1150, 860 cm$^{-1}$.

EXAMPLE 2

Anhydrous piperazine (86.2 g, 1 mole) and piperazine dihydrochloride (156.2 g, 1 mole) were dissolved in 1 liter of distilled water. Then, N-chloracetyl-cyclohexylamine (175.66 g, 1 mole) was added to the solution after which the preparation was completed as described in example 1.

EXAMPLE 3

Piperazine (258.6 g, 3 moles) were dissolved in 1 liter of distilled water and N-chloracetyl-cyclohexylamine (176.66 g, 1 mole) was thereafter added to this solution. Then, the preparation was completed as described in example 1.

EXAMPLE 4

Anhydrous piperazine (172.28 g, 2 moles) was dissolved in 1100 ml of water and 37% HCl (166.7 ml) was added dropwise under agitation to provide two moles of piperazine mono-hydrochloride.

Then, N(2-chloracetyl)-4-methyl-cyclohexylamine (190.7 g, 1 mole) was added to the solution whereby the temperature rose to 100° C. After refluxing for two hours the reaction was completed.

After cooling, the mixture was alkalinized with a 35% NaOH solution and extracted with $CHCl_3$. The chloroform solution was washed with water and dried with anhydrous $Na_2SO_4$; then it was filtered and evaporated. The residue was washed with petroleum ether, filtered and dried.

The product consisting in 1-piperazinyl-4-methylenecarbonyl-4'-methyl-cyclohexylamine (or N-(1-piperazinylacetyl)-4-methyl-cyclohexylamine), code C/82, was obtained in 70% yield based on theory.

Analysis: Calculated for $C_{13}H_{26}N_3O$: C 65.23; H 10.53; N 17.55; Found: C 65.15; H 10.41; N 17.68

EXAMPLE 5

Anhydrous piperazine (86.1 g, 1 mole) and piperazine dihydrochloride (156.2 g, 1 mole) were dissolved in 1100 ml of water. Then, N-(2-chloracetyl)-4-methyl-cyclohexylamine (19.7 g, 1 mole) was added and the reaction was completed as described in example 4.

Pharmacological properties of (C/63) and (C/82)

(1) Acute toxicity
(a) (C/63):
Mice DL/50   271    (311.6–235.6)   mg/kg
i.v.
Mice DL/50   1974   (2058.8–1892.6)
mg/kg os.
Rats DL/50   3900   (4251–3577.9)   mg/kg
os.
(b) (C/82):
Mice DL/50   1790   (1584–2022)   mg/kg
os.

(2) Sub-chronic toxicity (C/63)

Eighty Wistar rats were divided in 4 groups of twenty each (10 males and 10 fewales). Compound (C/63) was given per ora to three groups of animals for a period of 30 days in quantities of 100, 200 and 400 mg/kg. As a result, it was found that the rats which had been given an oral 400 mg/kg dose of (C/63) for 30 days showed no appearance of damages due to the toxicity of the drug as indicated by the checking of parameters such as bloodcrasis, biochemical blood analysis, weight and histological examination of the organs.

(3) Anti-ulcer activity
(a) Ulcer due to activity prevention (according to Rossi & Coll., C.P. Soc. Biol. 150, 2124 (1956)).

TABLE No 1

| Drug | Dose (mg/kg os.) | Inhibition % |
|---|---|---|
| C/63 | 50 | 19 |
| " | 100 | 32 |
| " | 200 | 45 |
| C/82 | 100 | 30 |
| " | 200 | 35 |

(b) Reserpine ulcer with rats (according to Radouco, Thomas & Coll., Arzneimittel Forschung 10, 588 (1966)).

TABLE No 2

| Drug | Dose (mg/kg os.) | Inhibition % |
|---|---|---|
| C/63 | 300 | 25 |
| C/82 | 100 | 47 |
| " | 300 | 70 |

(c) Phenylbutazone-histamine ulcer (according to Carminati & Coll., Boll. Chim Pharm. 112, 45 (1973)).

TABLE No 3

| Drug | Dose (mg/kg os.) | Inhibition % |
|---|---|---|
| C/63 | 25 | 10 |
| " | 50 | 43 |
| " | 100 | 72 |
| C/82 | 50 | 33 |
| " | 100 | 60 |

(d) Withdrawal ulcer (according to Adami & Coll., Arch. Int. Pharmacodyn. 147, 8 (1964)).

TABLE No 4

| Drug | Dose (mg/kg os.) | Inhibition % |
|---|---|---|
| C/63 | 100 | 33 |
| C/82 | 100 | 30 |

(e) Shay ulcer

TABLE No 5

| Drug | Dose (mg/kg os.) | Inhibition % |
|---|---|---|
| C/63 | 300 | 72 |

Activity on the gastric secretion (according to Shay, Gastroenterology 5, 43 (1945)).

TABLE No 6

| Drug | Dose | Modifications | | |
|---|---|---|---|---|
| | | Volume | pH | free HCl | total acid |
| C/63 | 100 | − 32 | + 60 | − 37 | − 13 |
| " | 200 | − 58 | + 117 | − 57 | − 25 |
| " | 300 | − 92 | + 150 | − 100 | − 55 |
| C/82 | 100 | − 37 | + 59 | − 19 | − 5 |

(4) Spasmolytic activity
(a) C/63
"In vitro"
Guinea-pig Ileus

C/63 has a $DE_{50}$ against Ach. histamine and $BaCl_2$ in excess of 40 mcg/ml.

"In vivo"

Activity of C/63 on intestine peristaltis (mouse)

TABLE No 7

| Drug | Dose (mg/kg os.) | Inhibition % |
|------|------------------|--------------|
| C/63 | 100 | 6 |
| " | 200 | 23 |

(b) C/82

The compound C/82 has no anticholinergic activity.

The present invention also concerns pharmaceutical compositions which may contain, according to the invention, the new compounds in admixtures with solid or liquid pharmaceutical diluents or carriers and, as desired, in admixtures with other active ingredients or binders.

As examples of pharmaceutical packages, one can mention 50 or 100 mg capsules and ampoules of C/63 or C/82. The daily dose will be 1 to 2 ampoules or 2 to 4 capsules.

I claim:

1. A compound of the formula

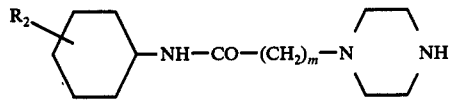

wherein $R_2$ is hydrogen or a lower alkyl group of from 1 to 6 carbon atoms and $m$ is 1 or 2.

2. N-cyclohexyl-1-piperazino acetamide.

3. N-4'-methyl-cyclohexyl-1-piperazino acetamide.

4. A pharmaceutical composition having antisecretory and antiulcer activity comprising a compound according to claim 1 together with a pharmaceutically compatible carrier.

5. A pharmaceutical composition having antisecretory and antiulcer activity comprising N-cyclohexyl-1-piperazino-acetamide in admixture with a pharmaceutical carrier.

6. A pharmaceutical composition having antisecretory and antiulcer activity comprising N-4'-methylcyclohexyl-1-piperazino-acetamide in admixture with a pharmaceutical carrier.

* * * * *